(12) United States Patent
Klug et al.

(10) Patent No.: US 7,787,118 B2
(45) Date of Patent: Aug. 31, 2010

(54) APPARATUS AND METHOD FOR OBTAINING SPECTRAL INFORMATION

(75) Inventors: David Rupert Klug, London (GB); Paul Murray Donaldson, London (GB)

(73) Assignee: Imperial Innovations Limited, London (GB)

( * ) Notice: Subject to any disclaimer, the term of this patent is extended or adjusted under 35 U.S.C. 154(b) by 0 days.

(21) Appl. No.: 12/302,085

(22) PCT Filed: May 23, 2007

(86) PCT No.: PCT/GB2007/001903

§ 371 (c)(1),
(2), (4) Date: Jan. 26, 2009

(87) PCT Pub. No.: WO2007/138267

PCT Pub. Date: Dec. 6, 2007

(65) Prior Publication Data

US 2009/0268200 A1    Oct. 29, 2009

(30) Foreign Application Priority Data

May 25, 2006    (GB) ................... 0610462.4

(51) Int. Cl.
*G01J 3/44* (2006.01)
(52) U.S. Cl. .................................... 356/301
(58) Field of Classification Search ............... 356/301, 356/445; 250/340, 338.1
See application file for complete search history.

(56) References Cited

U.S. PATENT DOCUMENTS

2003/0073139 A1* 4/2003 Kreimer et al. .............. 435/7.9

2004/0142484 A1* 7/2004 Berlin et al. ................ 436/171

FOREIGN PATENT DOCUMENTS

WO    2004031749    4/2004

OTHER PUBLICATIONS

Wei Zhao et al: "Doubly vibrationally enhanced four wave mixing: the optical analog to 2D NMR"; Physical Review Letters, New York, NY, US, vol. 84, No. 7, Feb. 14, 2000, pp. 1411-1414, XP002395438.
Raschke M B et al: "Doubly-resonant sum-frequency generation spectroscopy for surface studies"; Chemical Physics Letters, North-Holland, Amsterdam, NL; vol. 359, No. 5-6, Jun. 27, 2002, pp. 367-372, XP002395434.

(Continued)

*Primary Examiner*—Tarifur Chowdhury
*Assistant Examiner*—Abdullahi Nur
(74) *Attorney, Agent, or Firm*—Warner Norcross & Judd LLP

(57) ABSTRACT

A method of obtaining spectral information comprises initiating at least a first excitation at a first excitation frequency and a second excitation at a second frequency in a surface enhanced sample. The method further comprises varying one of said first and second excitation frequencies, detecting an output signal having an output signal strength and identifying an output signal peak. In addition the method includes correlating the identified output signal with the first and second excitation frequencies to obtain spectral information, in which the surface enhanced sample substrate is configured to enhance the field corresponding to at least one of the first and second excitation, or output fields initiated in this sample.

11 Claims, 1 Drawing Sheet

OTHER PUBLICATIONS

Figure 1:
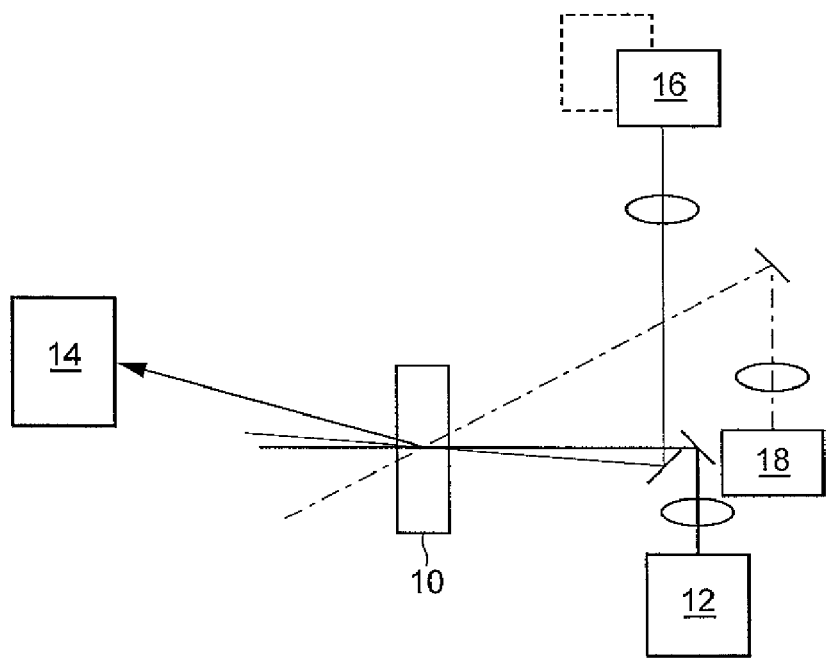

Bonn M et al: "Novel surface vibrational spectroscopy: Infrared-infrared-visible sum-frequency generation"; Physical Review Letters, New York, NY, US, vol. 86, No. 8, Feb. 19, 2001, pp. 1566-1569, XP002395435.

Ishibashi T et al: "Multiplex Sum-Frequency Spectroscopy with Electronic Resonance Enhancement"; Chemistry Letters, Nippon Kagakukai, Tokyo, JP, vol. 33, No. 11, 2004, pp. 1404-1407, XP008067944.

P.C. Lee and D. Meisel, "Adsorption and surface-enhanced Raman of dyes on silver and gold sols"; J. Phys. Chem. 86, 1982, p. 3391-3395.

L. Gunnarsson et. al., Interparticle coupling effects in nanofabricated substrates for surface-enhanced Raman scattering; Appl. Phys. Lett., vol. 78, p. 802, Feb. 5, 2001.

Muller et. al., Imaging the Thermodynamic State of Lipid Membranes with Multiplex CARS Spectroscopy; J. Phys. Chem. B., 2002, 106, 3715-3723.

John C. Wright, "Interference, dephasing, and vibrational coupling effects between coherence pathways in doubly vibrationally enhanced nonlinear spectroscopies" J. Chemical Physics, 2001, 266, p. 177-195.

Basic one- and two-dimensional NMR spectroscopy 4th edition, Published 2005, p. 231-288.

Written Opinion, International Application PCT/GB2006/001870, International Filing Date May 19, 2006.

International Search Report, International Application PCT/GB2006/001870, International Filing Date May 19, 2006.

Kent A. Meyer and John C. Wright, "Detection Limits for Time-Resolved Coherent Two-Dimensional Vibrational Spectroscopy", Analytical Chemistry 2001, vol. 73, p. 5020-5025.

W. M. Tolles, J. W. Nibler, J. R. McDonald and A. B. Harvey, "A Review of the Theory and Application of Coherent Anti-Stokes Raman Spectroscopy (CARS)"; Applied Spectroscopy, vol. 31, No. 4, 1977.

K Wolfrum, J Lobau, W Birkholzer and A Laubereau, "Vibrational sum-frequency spectroscopy of phase transitions in Langmuir films and three-colour pump-probe studies of chemisorbed molecules"; Quantum Semiclass. Opt. 9 (1997) p. 257-267.

S. Funk, M. Bonn, D. N. Denzler, CH. Hess M. Wolf and G. Ertl, "Desorption of CO from Ru(001) induces by near-infrared femtosecond laser pulses", Journal of Chemical Physics, vol. 112, No. 22, XP008067894.

Van Der Ham et al., "Giant enhancement of sum-frequency yield by surface-plasmon excitation", J. Optical Society of America, vol. 16, No. 7, Jul. 1999.

Chew et al, "Surface enhancement of coherent anti-Stokes Raman scattering by colloidal spheres", J. Optical Society of America, vol. 1, No. 1, Mar. 1984.

Alan Campion and Patanjali Kambhampati, "Surface-enhanced Raman scattering", Chemical Society Reviews, 1998, vol. 27.

* cited by examiner

APPARATUS AND METHOD FOR OBTAINING SPECTRAL INFORMATION

The invention relates to an Apparatus and Method for obtaining spectral information.

The use of the Raman effect for spectroscopic analysis is well known. In its simplest form the effect is observed when a laser beam is incident on a sample. Most of the incident light is elastically scattered, however a small population of photons is inelastically scattered as a result of excitation to or from a vibrational state and subsequent decay giving rise to a photon emitted at, respectively, a lower (Stokes) or higher (anti Stokes) energy. The difference in energy provides a measure of the energy of the vibrational modes of the sample molecule allowing provision of a Raman spectrum providing a powerful technique for identifying sample structure and composition.

Resonance Raman spectroscopy improves the sensitivity problem of 'ordinary' Raman spectroscopy by tuning a visible beam near an electronic resonance, increasing the scattered signal. Adding an additional visible beam to stimulate the scattering gives stimulated Raman scattering. In order to more easily distinguish the Raman scattered beam from the stimulating beam CARS (coherent anti-Stokes Raman scattering) has been developed according to which intense beam pulses provide a CARS signal at a different frequency to the input beams. CARS can be performed at non-resonant, resonance or 'pre-resonant'. Resonant CARS however suffers from non resonant background problems from non-sample material such as slide glass which limits sensitivity, especially when resonant.

In a further development it is found that a significantly enhanced response can be used in the case of Surface Enhanced Raman Spectroscopy (SERS) which is described in "Surface-Enhanced Raman scattering" by Campion et al, Chemicals Society Reviews, 1998, Volume 27, page 241 to 250 which is incorporated herein by reference. According to this technique it is found that enhancements in the Raman effect are detected for molecules bound to rough metal nano particles or surfaces because the surface enhances the incident laser field and therefore increases the Raman scattered field. For example in the case of nano-particles, the laser field drives plasmon oscillations in the nano particles and if the particles have rough edges, the field from the plasmons near these edges will be much higher than the incident laser field. When the particles have a plasmon resonance near the laser field frequency, the surface fields will be even larger. Thus the molecules experience a greater field at the surface of the particle and the Raman scattering is increased. Further discussion of such techniques is found in, for example, "a Surface Enhancement of Coherent Anti-stokes Raman Scattering by Colloidal Spheres" of Chew et al, J. Opt. Soc. Am B/Vol. 1, No. 1/March 1984, pages 56-66, and "Giant Enhancement of Sum-Frequency Yield by Surface-Plasmon Excitation" of Vander Ham et al, J. Opt. Soc. Am B/Vol. 16, No. 7/July 1999 pages 1146 to 1152.

In all of these arrangements, whilst increased sensitivity is provided, limited spectral information is available using surface enhanced spectroscopy such as surface enhanced Raman spectroscopy.

The invention is set out in the claims. Because first and second variable wavelength excitation beams are incident on a surface enhanced configuration, the output spectral information allows multi-dimensional information about the spectrum to be derived.

Figure 2:
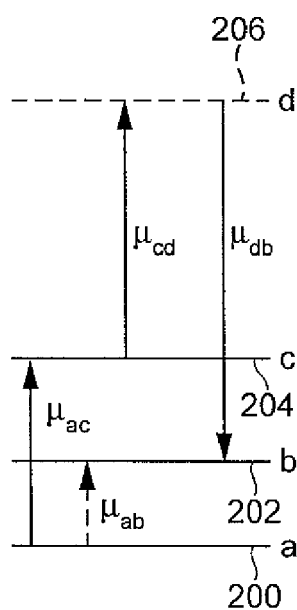

The invention will be described further, by way of example, with reference to the drawings of which:

FIG. 1 shows an apparatus for performing a method of spectroscopy according to the present invention; and FIG. 2 is a diagram showing transitions in a four-waves mixing interaction.

In overview a multi-dimensional spectroscopy is provided. The method obtains additional spectral information by applying multiple excitations to a sample prepared for surface enhanced spectroscopy for example a sample molecule adsorbed on to an appropriate surface or surface substrate such as silver, or on to the surface of an nano particle. The spectral information obtained can be analysed using, for example, two dimensional spectroscopy techniques such as plotting the spectra in the frequency domain for each excitation against one another on respective axis. From the surface thus obtained, detailed information concerning the structure of the sample can be derived.

For example first and second excitation beams are provided incident on the sample at respective first and second wavelengths $\omega_1$ and $\omega_2$ which are preferably different from one another and can be for example in the infrared. As a result a vibrational coherence is induced in the sample generating a combination excitation band which is shown as energy band c in FIG. 2. A third excitation beam $\omega_3$ in which can be in the visible is incident on the beam providing a scattered output beam $\omega_4$ at a different frequency from each of $\omega_1$ to $\omega_3$ as a result of a Raman-like transition from a virtual, potentially pre-resonant state d (206) to a vibrational level b (204).

As discussed in more detail below, variation of at least one of $\omega_1$ and $\omega_2$ varies the combination band level. When $\omega_4$ hits a resonance, that is, returns a larger signal, this provides information about $\omega_1$ and $\omega_2$. In particular the resonance can be plotted against $\omega_1$ and $\omega_2$ and the various resonances indicated on such a plot can provide a molecular "fingerprint" of the sample. It will be noted that the effect is enormously enhanced by the surface—enhanced configuration which is tuned, for example, between then and typically tailored to enhance at least one of $\omega_3$ and $\omega_4$ (and often both as they may well be embraced by the same enhancement band). In addition or alternatively enhancement can also be achieved in relation to $\omega_1$ or $\omega_2$ again providing significant additional information in a surface-enhanced spectroscopy. As a result a strong signal can be obtained even for low sample concentration.

Referring to FIG. 1 an apparatus for obtaining multi-dimensional surface enhanced spectroscopy is shown in a transmission mode generally as including a sample 10, excitation sources comprising lasers 12, 18 emitting radiation typically in the infrared band and a detector 14. Tuneable lasers 12 and 18 emit excitation beams of, for example, respective wavelengths/wavenumbers 3164 cm$^{-1}$ ($\omega_1$) and 2253 cm$^{-1}$ ($\omega_2$) which excite one or more vibrational modes of the molecular structure of the sample 10 and allow multi-dimensional data to be obtained by tuning the frequencies or providing variable time delays. A third excitation or read-out beam is generated by a third laser 16 to provide an output or read out in the form of an effectively scattered input beam, frequency shifted (and strictly generated as a fourth beam) by interaction with the structure of sample 10. The frequency ($\omega_3$) of the third beam preferably lies in the visible range and may be variable or fixed, for example at 795 nm, as is discussed in more detail below. The detected signal is typically in the visible or near infrared part of the electromagnetic spectrum e.g. at 740 nm, comprising photons of energy from infrared to ultra-violet.

Although the invention is referred to herein as using tuneable lasers 12 and 18 to excite one or more vibrational modes of the sample 10, it will be appreciated by the skilled person that this terminology also encompasses inducing vibrational coherences within the sample 10.

In order to obtain multi-dimensional data, the sample is excited by successive beams spaced in the time domain. However any appropriate multi-dimensional spectroscopic technique can be adopted, for example by varying the input in the frequency domain rather than the time domain. Similarly any number of dimensions can be obtained by additional pulses in the time domain or additional frequencies in the frequency domain. Of course the arrangement can also be provided in any of a transmission or reflection form and, for example, using co-linear beams.

A two dimensional spectroscopy method of the type described above is set out in, for example, International application no. PCT/GB2004/004693 which is commonly assigned herewith and which is incorporated herein by reference. Further discussion of two dimensional spectroscopy in the field of nuclear magnetic spectroscopy (NMR) those teachings can be applied similarly is described in Friebolin, "Basic one- and two-dimensional NMR spectroscopy" $2^{nd}$ edition (April 1993) John Wiley & Sons, incorporated herein by reference.

The sample and/or sample substrate itself can be prepared in any appropriate manner to obtain surface enhanced multi-dimensional spectroscopy (SEMS). In one embodiment a nanoscopic substrate is engineered having plasmon oscillations at the laser excitation frequencies. Coinage metals can be used either in the form colloidal suspension, roughened electrochemical tips or sculpted surfaces ensuring that the surface chemistry of both the analyte and the substrate is engineered in such a manner that the analyte will stably bind to the substrate as interaction between the analyte and the nano particles must be strong enough to avoid aggregation of the nano particles and/or aggregation of the analyte. For example the substrate may be coated with another material to allow it to bind specific analytes.

Preparation of the colloidal sample can be carried out in any conventional manner as will be apparent to the skilled person such that detailed description is not required here. For example the citrate reduction of silver nitrate method can be applied as described in P. C. Lee and D. Meisel, J. Phys. Chem 86, p 3391, 1982. Similarly the surface can be prepared in any appropriate manner for example as described in L. Gunnarsson et al, Appl. Phys. Lett 78, p 802, 2001. The techniques described in those references are incorporated herein by reference.

In order to best engineer the sample it is necessary to ensure that the sample has a thickness appropriate for phase matching, that plasmon resonance frequencies coincide with one of the multi-wave mixing frequencies $\omega_1$, $\omega_2$, $\omega_3$, $\omega_4$.

The level of enhancement provided by a combination of multi dimensional spectroscopy and surface enhanced spectroscopy can be further understood from a discussion of the underlying physical mechanisms.

The effect in fact relies on a four wave mixing methodology. Four wave mixing occurs in a polarisable medium when three time varying fields of sufficient strength induce a non-linear polarisation that oscillates at a frequency $\omega_4$.

$$\omega_4 = \omega_1 \pm \omega_2 \pm \omega_3 \quad (1)$$

In the case of Raman spectroscopy, the interaction occurs between a single beam interacting with two additional fields created by a black body photon which create the perturbations in the energy levels which give rise to inelastic scattering. In stimulated Raman scattering, one of the additional fields is instead provided by the resonance beam. As discussed above, by carrying out Raman spectroscopy on the sample surface of a substrate, these fields are enhanced by the local electric field at the surface.

In the case of the excitation scheme described according to the present invention, $\omega_1$ and $\omega_2$ are generated by external laser beams in the architecture described above, preferably in the infrared range, with each laser 12, 18 being tuned to a separate vibrational resonance of the sample 10. The third laser 16 produces a beam of frequency $\omega_3$ which preferably lies in the in the visible range. If $\omega_3$ lies in the visible range, $\omega_4$ produced can also lie in the visible range, making it detectable by a simple method of photon counting.

The polarisation described above hence launches a field that also oscillates at $\omega_4$. In practice the fields used to create $\omega_4$ are sub-nanosecond laser pulses. The different signs in equation 1) yield various $\omega_4$ frequencies and can be selected by introducing angles between the laser pulses (phase matching) such that the required $\omega_4$ is selected by momentum conservation rules or spectral dispersion of the output signals.

As discussed above, four wave mixing becomes a spectroscopy when one or more of the laser fields are tuned in frequency $\omega_{laser}$ through an electronic or vibrational resonance feature of the sample 10 probed. The polarisation becomes very large around a resonance and the four wave mixing signal increases as:

$$E_4 \propto \sum_{resonances, lasers} \frac{A}{\overline{\omega}_{res} - \overline{\omega}_{laser} - i\Gamma} \quad (2)$$

A is a constant, $\omega_{res}$ is the frequency of the resonance and $\Gamma$ is the lifetime of the induced polarisation.

In a preferred embodiment, the invention uses Doubly Vibrationally Enhanced four wave mixing (DOVE-FWM), as described by Wei Zhao and John C Wright in "Phys. Rev. Lett, 2000, 84(7), 1411-1414". DOVE-FWM occurs when $\omega_1$ and $\omega_2$ are resonant with coupled vibrations within the sample, $v_1$, $v_2$ and $v_3$. In this case the signal increases as:

$$E_4 \propto \frac{A_{DOVE-IR}}{(\overline{\omega}_{v_1} - \overline{\omega}_1 - i\Gamma_{v_1 g})(\overline{\omega}_{v_2} - \overline{\omega}_2 - \Gamma_{v_2 g})} + \frac{A_{DOVE-RAMAN}}{(\overline{\omega}_{v_1} - \overline{\omega}_1 - i\Gamma_{v_1 g})(\overline{\omega}_{v_3} - (\overline{\omega}_1 - \overline{\omega}_2) - i\Gamma_{v_3 g})} \quad (3)$$

The signals here are products of resonance terms and hence larger than the sum of resonance terms in Equation 2. Mapping the signal for all combinations of $\omega_1$ and $\omega_2$ gives a 2D map of coupled vibrations in the material probed.

Because the output beam produced is of a different frequency, $\omega_4$, to any of the input beams, and a strong signal is produced by DOVE-FWM, therefore it is easily detected.

A representative energy level diagram is shown in FIG. 2 including a ground state 200, a vibrational level 202, a combination band 204 and virtual, potentially pre-resonant state 206 in order of increasing energy. As a result four possible transitions are available, where the ground state, vibrational level, combination band and virtual state are labelled a, b, c, d respectively: $\mu_{ab}$, $\mu_{ac}$, $\mu_{cd}$, $\mu_{db}$, where $\mu$ is the transition dipole moment. The intensity of a four-wave mixing signal can be expressed.

$$I(t) = \frac{16\pi^2 \bar{\omega}_4^2 L^2 F}{n_{\bar{\omega}_4} c^4 \varepsilon_0^4} |\chi^{(3)}|^2 I_1 I_2 I_3 \frac{\sin^2(\Delta k L)}{(\Delta k L/2)^2} \quad (4)$$

With³

$$\chi^{(3)} = \frac{NF' \mu_{ac} \mu_{ab} \mu_{cd} \mu_{db}}{8\hbar^3 \Delta_{ca} \Delta_{ba} \Delta_{da}} \rho_{aa} \quad (5)$$

So for a thin sample ($\Delta k=0$) we have $$I(t) \propto L^2 N^2 \bar{\omega}_4^2 I_1 I_2 I_3 \left| \frac{\mu_{ac} \mu_{ab} \mu_{cd} \mu_{db}}{\Delta_{ca} \Delta_{ba} \Delta_{da}} \right|^2 \quad (6)$$

Where N is the concentration of analyte, L is the sample thickness and F/F' are local field correction factors which are typically 1-2, $\Delta_{ij}$ are the frequency dependent detuning factors$=\omega_{ga}-\omega_{laser}-i\Gamma_{ga}$, $\Gamma_{ga}$ is the coherence lifetime and $\Delta k$ is the phase mismatch of the sample. This is the difference between the momentum of the input beams and the momentum of the output, corrected for variations in refractive index.

$\mu_{ab}$ and $\mu_{ac}$ comprise the infrared transition dipole moments for linear absorption for the fundamental and combination bands $\mu_{ed}$ and $\mu_{db}$ are the electric transition dipole moments for Raman-like transitions. 'In' as much as the frequency differs from the input frequency' it will be appreciated that the same effects can be observed in DOVE-FWN whether the excitation are timed and ordered to produce DOVE-Raman or DOVE-IR configurations.

Where the source produces coherent excitation readout beams, such as in the configuration described above it will be noted that any enhancement is squared providing a surprisingly high enhancement factor as well as the ability to accurately select the desired interaction "pathway" to produce a desired form of FWM.

The approaches described above can be applied in relation to homodyne or heterodyne spectroscopy. By way of definition, all spectroscopic methods including the present invention emit a signal whose intensity can be defined as follows:

$$I=(E_{LO})^2+(E_{HO})^2+(E_{LO} \times E_{HO})\cos \phi \quad (7)$$

Here, $E_{HO}$ is the homodyne signal from the sample and $E_{LO}$ is a "local oscillator" field. The two fields are of the same frequency but have a fixed phase difference $\phi$. In standard homodyne detection, there is no local oscillator field, and the intensity is simply the homodyne term $E_{HO}^2$, which varies quadratically with the concentration of the sample. In heterodyne detection, a separate local oscillator is created and manipulated by any known method as will be apparent to the skilled reader, so that the cross term can be made to dominate the equation. The output field is then linear in sample concentration. This may be used in certain embodiments in which the sample concentration is low and it is desirable to produce a stronger output signal.

For example conventional optical heterodyne can be adopted In a further approach, conventional optical heterodyning can be adopted in which a local oscillator field is created external to the sample and directed to be incident on the detector with the sample field. Such local oscillator generation may be by, for instance, continuum generation in a suitable liquid or solid with a portion of the visible beam. In that case the specific parameters of the external signal are controlled so that the relevant terms dominate in equation (1) above, in contrast to conventional optical heterodyning systems where the linear contribution is swamped as discussed in more detail above. Removal of the $(E_{LO})^2$ term is then simply achieved using a lock-in detector whereby a mechanical wheel with slots in it ("a chopper") is introduced into an excitation beam. The repetition rate with which the slots block the beam (reference frequency) is passed to a lock-in detector, which is basically a frequency filter—it measures the total net signal coming from the detector and extracts the component of the signal which occurs at the reference frequency. If the reference frequency is different from the repetition rate of the beam which causes the local oscillator signal, the component of the net signal due exclusively to the local oscillator is subtracted off. Then, the $E_{LO}^2$ term disappears, the $E_{HO}^2$ term is negligible, and the cross term is linear in concentration.

In a further embodiment, "multiplexing" of the type described in Muller et al, "Imaging the Thermodynamic State of Lipid Membranes with Multiplex CARS Spectroscopy" J. Phys. Chem. B. 106, 3715-3723, which is incorporated by reference, is achieved by the use of broadband pulses in the infrared, created by ultrafast pulses to simultaneously excite infrared transitions in the sample and the spectral portions surrounding them. By appropriate selection of the input angles of the beams, unique directions corresponding to input frequencies can be achieved. As a result the output signal is a cone of rays containing all of the spectral information in space; the detector 14 can in this case be a 2D array detector such as a charge coupled device (CCD) which captures the spectral information encoded into spatial dimensions. Once again to obtain improved resolutions of spectra, in addition to the spatial dimensions, additional dimensions are introduced either by time delays in the pulses or by frequency variations as discussed in more detail above to give yet further, fully detailed information concerning the spectrum generated by the sample.

In one embodiment $\omega_1$ and $\omega_2$ are selected to give DOVE-FWM and $\omega_3$ is tuned near an electronic resonance of excitation frequency $\omega_e$. If the electronic resonance is coupled to the vibrations that $\omega_1$ and $\omega_2$ probe, a further multiplicative enhancement can be made to both terms in Equation 3). The technique will give a 3D map of electronic/vibrational coupling. For example, the DOVE-IR case becomes:

$$E_4 \propto \frac{A_{DOVESE-IR}}{(\bar{\omega}_{v_1} - \bar{\omega}_1 - i\Gamma_{v_1 g})(\bar{\omega}_{v_2 g} - \bar{\omega}_2 - i\Gamma_{v_2 g})(\bar{\omega}_e - \bar{\omega}_3 - i\Gamma_e)} \quad (8)$$

If the vibrations probed by $\omega_1$ and $\omega_2$ are not coupled to the electronic state, the electronic enhancement is described by Equation 2) and therefore much weaker than that of Equation 5).

Delays between the laser pulses suppress non resonant or singly resonant signals and select the various possible FWM signals of interest. This method is discussed further by John Wright in "J. Chem. Phys, 2001, 266, 177-195". No existing technique takes advantage of the strong electronic absorption of visible laser light for use in 2 or more dimensional vibrational spectroscopy whilst providing strong output signals and minimal non resonant background noise.

In a further, alternative embodiment where heterodyning is not used, an ultraviolet or visible excitation excites an electronic resonance which in turn gives rise to fluorescence caused by transitions between electronic energy levels. This is in combination with direct infrared excitation of the type discussed above. In that case the additional "read out" signal from laser 16 is not required. Tuning of input infrared and ultraviolet beams and varying time delays yields multi-dimensional data again in a manner described in more detail above, but based on a population spectroscopy.

When reflective mode spectroscopy is employed, it will be appreciated by the skilled person that the reflection is not limited to the surface of the sample and therefore that this terminology also encompasses evanescent mode spectroscopy. The nature of the reflected signal produced will vary according to input beam penetration depth. Factors which determine the penetration depth include the angle of incidence of the third frequency input beam and the polarisation of the field.

The invention can be implemented in a range of applications and in particular any area in which multi-dimensional optical spectroscopy measuring, directly or indirectly, vibration/vibration coupling is appropriate, using two or more variable frequencies of light or time delays to investigate molecular identity and/or structure The skilled person will recognise that any appropriate specific component and techniques can be adopted to implement the invention. Typically at least one tuneable laser source in the infrared and at least one other tuneable laser source in the ultraviolet, visible or infrared can be adopted and any appropriate laser can be used or indeed any other appropriate excitation source. A further fixed or tuneable frequency beam may also be incorporated in the case of two infrared excitation beams as discussed above. Alternatively, a commercial sub-nanosecond laser system for FWM experiments can be used to generate separate frequencies from a single laser seed source including three independently tuneable beams.

Any appropriate detector may be adopted, for example a CCD or other detector as is known from 2D IR spectroscopy techniques.

The range of excitation wavelengths produced by lasers 12 and 18 is generally described above as being infrared but can be any appropriate wavelength required to excite a vibrational mode of the structure to be analysed. Similarly, the wavelength produced by third laser (16) is generally described as being visible but can be any appropriate wavelength required to excite an electronic resonant mode of the structure to be analysed. Although the discussion above relates principally to two or three-dimensional analysis, any number of dimensions can be introduced by appropriate variation of the parameters of the input excitation, for example frequency, time delay/number of pulses or any other appropriate parameter.

Although four-wave mixing is described, alternatively other modes such as three wave mixing may be implemented in which case the output is in the rear infrared.

The invention claimed is:

1. A method of obtaining spectral information comprising:
    using a first excitation beam at a first excitation frequency and a second excitation beam at a second, different excitation frequency to initiate at least a first excitation and a second excitation in a surface—enhanced sample;
    using a third excitation beam at a third excitation frequency to initiate a third excitation;
    varying the excitation frequency of one of the first and second excitation beams;
    detecting an output signal having an output signal frequency that is different to each of said first, second an third excitation frequencies;
    identifying an output signal peak; and
    correlating the output signal peak with the first and second excitation frequencies to obtain spectral information on the sample;
    in which the surface enhanced sample substrate is configured to enhance the field corresponding to at least one of the first, second and third excitation beams, or to enhance an output field initiated in the sample.

2. A method as claimed in claim 1 in which at least one of the first and second excitation beam has a respective excitation frequency in the infrared part of the spectrum.

3. A method as claimed in claim 1 in which the excitations are initiated by respective coherent excitation beam sources.

4. A method as claimed in claim 1 in which the third excitation beam has an excitation frequency in the visible part of the spectrum.

5. A method as claimed in claim 4 in which the surface enhanced sample substrate is tuned for surface enhancement in the visible part of the spectrum.

6. A method as claimed in claim 1 in which a plasmon resonance frequency of the substrate coincides with at least one of the excitation frequencies or the output signal frequency.

7. A spectroscopy apparatus comprising:
    a first excitation source arranged to initiate a first excitation in a sample;
    a second excitation source arranged to initiate a second, different excitation in the sample;
    a third excitation source arranged to initiate a third excitation in the sample; and
    a detector arranged to detect an output beam from the sample at a frequency that is different to the respective frequencies produced by the first, second and third excitation sources;
    in which the sample is configured to enhance the field corresponding to at least one of the excitations or to enhance an output field induced in the sample.

8. An apparatus as claimed in claim 7 further comprising a controller for controlling variation of the frequency of at least one of the first and second excitation sources.

9. An apparatus as claimed in claim 7 in which the apparatus is arranged to generate an output beam in one of a transmissive or reflective mode.

10. An apparatus as claimed in claim 7 in which the first and second excitation sources are coherent sources.

11. An apparatus as claimed in claim 7 wherein the sample is a substrate and has an enhanced surface configured to enhance the field corresponding to at least one of an excitation or output field in a multi dimensional spectroscopy apparatus.

* * * * *